United States Patent [19]
Lin et al.

[11] Patent Number: 5,470,862
[45] Date of Patent: Nov. 28, 1995

[54] SUBSTITUTED PYRAZOLYL COMPOUNDS AND METHODS EMPLOYING SUCH COMPOUNDS

[75] Inventors: Bor-Sheng Lin, Berkeley Heights; Joseph W. Scheblein, Flemington; Jerome R. Bagley, North Plainfield, all of N.J.

[73] Assignee: Ohmeda Pharmaceutical Products Division Inc., Liberty Corner, N.J.

[21] Appl. No.: 384,294

[22] Filed: Feb. 3, 1995

[51] Int. Cl.⁶ .................. A61K 31/41; A61K 31/44; C07D 213/06
[52] U.S. Cl. .................. 514/341; 514/340; 514/342; 514/255; 546/279; 546/275; 546/276; 546/277; 544/405
[58] Field of Search .................. 546/279, 275, 546/276, 277; 514/341, 340, 342, 255; 544/405

[56] References Cited

PUBLICATIONS

Austo J. Chem. 39(10) pp. 1525–1536, 1986, Chiral . . . –pyrazoles, House et al.
CA106: 26888c Chiral . . . and –pyrazoles. House et al. p. 557, 1987.
CA108: 94546f Preparation . . . intermediates. Baba et al., p. 662, 1988.
CA118: 124407n Preparation . . . herbicides. Auinbauh et al., p. 795, 1993.

Primary Examiner—Joseph K. McKane
Attorney, Agent, or Firm—R. Hain Swope; Larry R. Cassett

[57] ABSTRACT

This invention pertains to novel substituted pyrazolyl compounds useful as intravenous anesthetics represented by the Formula:

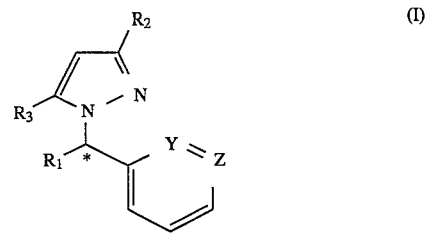

including geometric and optically active isomeric forms, and the pharmaceutically acceptable acid addition salts thereof, wherein:

one of Y and Z is nitrogen, and the other is CH;

$R_1$ is hydrogen or lower-alkyl;

$R_2$ and $R_3$ are selected from the group consisting of hydrogen, —CHO, lower-alkylcarbonyl, lower-alkoxy carbonyl, lower-alkylaminocarbonyl, lower-alkyl, lower-alkenyl, lower-alkoxy-lower-alkenyl, lower-alkylcarbonyloxymethyl, substituted and unsubstituted heterocyclic rings, and substituted or unsubstituted aryl groups, wherein the symbol * represents a carbon atom which may be asymmetric and at least one of $R_2$ and $R_3$ is other than hydrogen.

20 Claims, No Drawings

SUBSTITUTED PYRAZOLYL COMPOUNDS AND METHODS EMPLOYING SUCH COMPOUNDS

BACKGROUND OF THE INVENTION

1. Field of the Invention

The present invention relates to substituted pyrazolyl compounds, and pharmaceutical compositions and methods employing such compounds.

2. Description of the Background

European patent application no. 418,845A1 discloses certain substituted pyrazole derivatives having antiinflammatory, analgesic, and antithrombotic activity. The substituted pyrazole derivatives may be represented by the Formula:

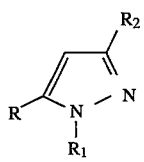

wherein $R_1$ is aryl which may be substituted with lower-alkyl, halogen, lower-alkoxy, lower-alkylthio, lower-alkylsulfinyl, lower-alkylsulfonyl, hydroxy, lower-alkylsulfonyloxy, nitro, amino, lower-alkylamino, acylamino, lower-alkyl(acyl)amino, or a heterocyclic group; $R_2$ is hydrogen, methyl substituted with amino, lower-alkylamino, halogen or acyloxy, acyl, acylamino, cyano, halogen, lower-alkylthio, lower-alkylsulfinyl, or a heterocyclic group; and $R_3$ is aryl substituted with lower-alkyl, lower-alkylthio, lower-alkylsulfinyl, halogen, amino, lower-alkylamino, acylamino, lower-alkyl(acyl)amino, lower-alkoxy, cyano, hydroxy, or acyl; or a heterocyclic group which may be substituted with lower-alkylthio, lower-alkylsulfinyl, or lower-alkylsulfonyl. There is no disclosure of substituted pyrazole derivatives having a carbon atom separating the pyrazole ring from the $R_1$ group.

SUMMARY OF THE INVENTION

This invention pertains to novel substituted pyrazolyl compounds useful as anesthetics, and methods of administering anesthesia, which comprises the systemic administration to mammals of such compounds, and pharmaceutical compositions containing such compounds. The novel compounds may be represented by the Formula:

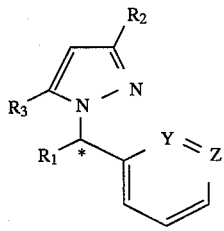

including geometric and optically active isomeric forms, and pharmaceutically acceptable acid addition salts thereof, wherein:

one of Y and Z is nitrogen, and the other is CH;

$R_1$ is hydrogen or lower-alkyl;

$R_2$ and $R_3$ are selected from the group consisting of hydrogen, —CHO, lower-alkylcarbonyl, lower-alkoxycarbonyl, lower-alkylaminocarbonyl, lower-alkyl, lower-alkenyl, lower-alkoxy-lower-alkenyl, lower-alkylcarbonyloxymethyl, substituted and unsubstituted heterocyclic rings, and substituted or unsubstituted aryl groups, wherein the symbol * represents a carbon atom which may be asymmetric and at least one of $R_2$ and $R_3$ is other than hydrogen.

DETAILED DESCRIPTION OF THE INVENTION

The substituted pyrazolyl compounds of the present invention possess very desirable anesthetic activities by intravenous administration. Many of the substituted pyrazolyls exhibit potent anesthesia in animals characterized by rapid onset, short duration of action, and quick recovery.

As set out above, the anesthetic compounds of the present invention have the general Formula (I):

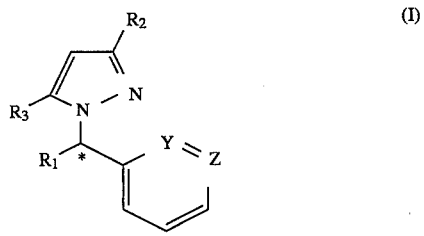

including geometric and optically active isomeric forms, and pharmaceutical acceptable acid addition salts thereof, wherein:

One of Y and Z is nitrogen, and the other is CH. Hence, Y and Z are members of a 2-pyridinyl or 3-pyridinyl ring. In a preferred embodiment, Y is nitrogen and Z is CH;

$R_1$ is hydrogen or lower-alkyl. Preferably, $R_1$ is hydrogen or methyl; and $R_2$ and $R_3$ are selected from the group consisting of hydrogen, —CHO, lower-alkylcarbonyl (e.g., —COCH$_2$CH$_3$), lower-alkoxycarbonyl (e.g., —COOCH$_2$CH$_3$), lower-alkylaminocarbonyl (e.g., —CONHCH$_2$CH$_3$), lower-alkyl, lower-alkenyl, lower-alkoxy-lower-alkenyl, lower-alkylcarbonyloxymethyl (e.g., —CH$_2$OOCCH$_3$), substituted or unsubstituted heterocyclic rings, and substituted or unsubstituted aryl groups. At least one of $R_2$ and $R_3$ is other than hydrogen. In a preferred embodiment, $R_3$ is —COOCH$_2$CH$_3$.

As utilized herein, the term "lower-alkyl", and the lower-alkyl portion of "lower-alkoxy", refers to branched- and unbranched-hydrocarbon groups containing from 1 to 6, preferably from 2 to 5 carbon atoms. The term "lower-alkenyl", as used herein, refers to branched and unbranched unsaturated hydrocarbon groups containing from 1 to 6, preferably from 2 to 5 carbon atoms. The lower-alkyl group may be unsubstituted or substituted with one or more members selected from the group consisting of oxo, hydroxyl, thio, and halogen. The term "halogen", as used herein, refers to the chemically related elements consisting of fluorine, chlorine, bromine and iodine.

Heterocyclic rings represented by $R_2$ and $R_3$ may be selected from the group consisting of monocyclic or fused bicyclic heterocyclic rings each having 5 to 6 ring member atoms. Each heterocyclic ring may contain from one to three heteroatoms selected from the group consisting of nitrogen, sulfur and oxygen.

Suitable heterocyclic rings represented by $R_2$ and $R_3$ include furanyl, thiophenyl, pyrrolyl, oxazolyl, isoxazolyl, thiazolyl, 2-(2-pyridinyl)thiazolyl, 2-(3-pyridinyl)thiazolyl, 1,2,4-oxadiazolyl, 1,3,4-oxadiazolyl, pyridinyl, and imidazo[1,2-a]pyridinyl. Preferred heterocyclic rings represented by $R_2$ and $R_3$ include furan-2-yl, furan-3-yl, thiophen-2-yl, thiophen-3-yl, pyrrol-2-yl, pyrrol-3-yl, (N-methyl)pyrrol-2-yl, (N-methyl)pyrrol-3-yl, oxazol-2-yl, oxazol-4-yl, oxazol-5-yl, isoxazol-3-yl, isoxazol-4-yl, isoxazol-5-yl, thiazol-5-yl, 2-(carboethoxy)thiazol-5-yl, 2-(2-pyridinyl)thiazol-5-yl, 2-(3-pyridinyl)thiazol-5-yl, 1,2,4-oxadiazol-5-yl, 1,3,4-oxadiazol-5-yl, pyridin-2-yl, pyridin-3-yl, pyridin-4-yl, and imidazo[1,2-a]pyridin-2-yl.

The heterocyclic rings represented by $R_2$ and $R_3$ may be substituted with one or more substituents independently selected from the group consisting of halogen, hydroxyl, nitro, amino, lower-alkoxy carbonyl, lower-alkyl, lower-cycloalkyl, lower-alkoxy, lower-thioalkyl, halogenated lower-alkyl, aryl, substituted aryl, and 5- or 6-member heterocyclics. In a preferred embodiment, the substituents are independently selected from the group consisting of a halogen, hydroxyl, nitro, amino, ethoxycarbonyl, methyl, ethyl, isopropyl, methoxy, thiomethyl, trifluoromethyl, phenyl and morpholinyl. Suitable substitutents for aryl groups represented by $R_2$ and $R_3$ are independently selected from the group consisting of halogen, lower-alkoxy, and lower-alkyl.

The compounds of the present invention which have at least one asymmetric carbon atom can exist in optically active isomeric forms. For example, in compounds in which $R_1$ is methyl, the carbon adjacent to $R_1$ is an asymmetric carbon atom (wherein the symbol * represents the asymmetric carbon atom) and such compounds can therefore exist in optical active isomeric (enantiomeric) forms, generally designated as R or S configurations. Such isomeric forms can be prepared by enantioselective (asymmetric) synthesis or can be isolated from racemic mixtures by separation techniques known to those skilled in the art.

The compounds of the present invention can also exist in geometrically isomeric forms because at least one of $R_2$ and $R_3$ is other than hydrogen. Although such compounds can be used as a mixture of such forms, it is often desirable to resolve the geometrically isomeric mixture because one form is more active or has other desirable characteristics. This resolution can be accomplished by techniques conventional in the art for such purpose, such as column chromatography or high pressure liquid chromatography or simple recrystallization.

The compounds of the present invention can be prepared by various methods. In general, the desired compounds represented by Formula I can be prepared by the methods illustrated in Schemes I through X set out below, wherein the substituents Y, Z, $R_1$, $R_2$, and $R_3$ have the definitions set out above.

Scheme I illustrates the synthesis of compounds represented by Formula IV. Oxidation of propargyl alcohol with chromium trioxide affords propargyl aldehyde which is reacted with ethyl diazoacetate to yield the corresponding pyrazole derivative. Alkylation of the pyrazole derivative with a compound such as 2-(alpha-bromoethyl)pyridine (II) yields isomers IIIa and IIIb. Oxazoles IVa and IVb can be prepared by reaction of isomers IIIa and IIIb with tosylmethyl isocyanide, respectively.

Scheme II illustrates the synthesis of compounds represented by Formula V. Reaction of 2-pyridylacetylene and ethyl diazoacetate yields 3-ethoxycarbonyl-5-(2-pyridyl)pyrazole. Alkylation of 3-ethoxycarbonyl-5-(2-pyridyl)pyrazole with 2-(alpha-bromoethyl)pyridine (II) affords isomers Va and Vb.

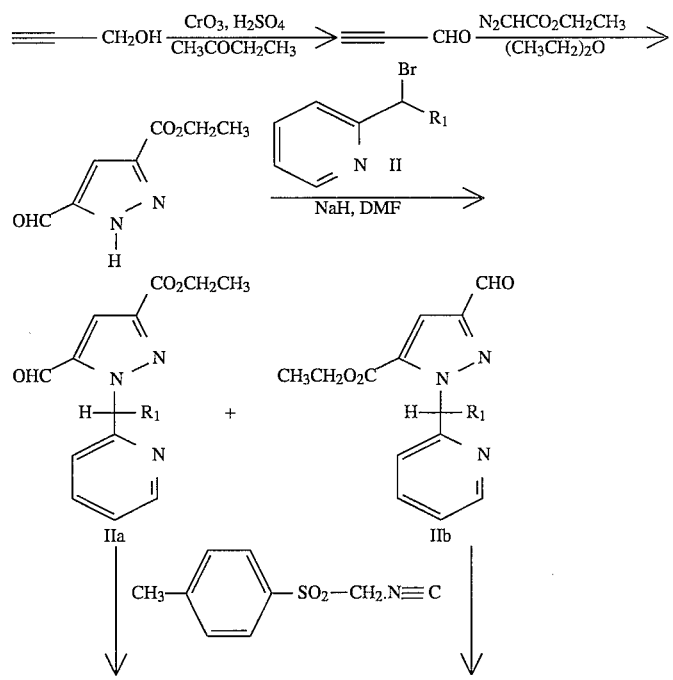

Scheme I

-continued
Scheme I

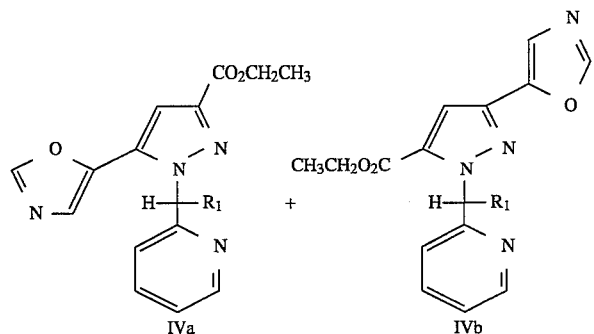

Scheme II

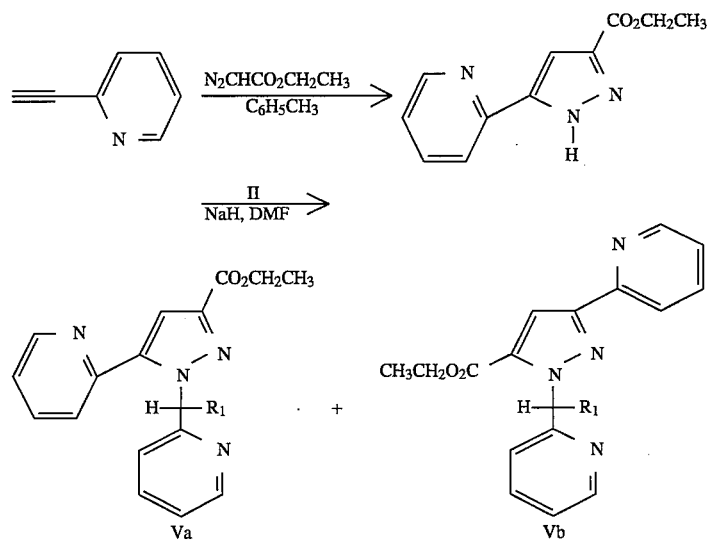

Scheme III illustrates the synthesis of compounds represented by Formulas VI and VII. Reaction of 3-butyn-2-one and ethyl diazoacetate yields 3-ethoxycarbonyl-5-acetylpyrazole which is brominated to yield the corresponding alpha-bromoacetyl derivative. Reaction of this alpha-bromoacetyl derivative with thioacetamide yields 3-ethoxycarbonyl-5-(2-methylthiazol-4-yl)pyrazole. Reaction of this alpha-bromoacetyl derivative with thiourea yields 2-aminothiazolyl. Alkylation, as described above, of 3-ethoxycarbonyl-5-(2-methylthiazol-4-yl)pyrazole with 2-(alpha-bromoethyl)pyridine (II) yields isomers VIa and VIb. Whereas alkylation of 2-aminothiazolyl yields isomers VIIa and VIIb.

Scheme III

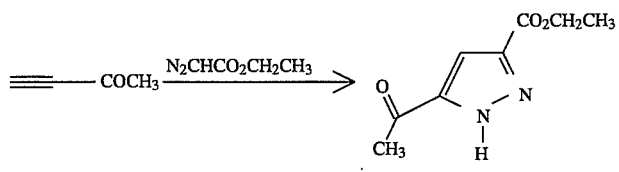

-continued
Scheme III

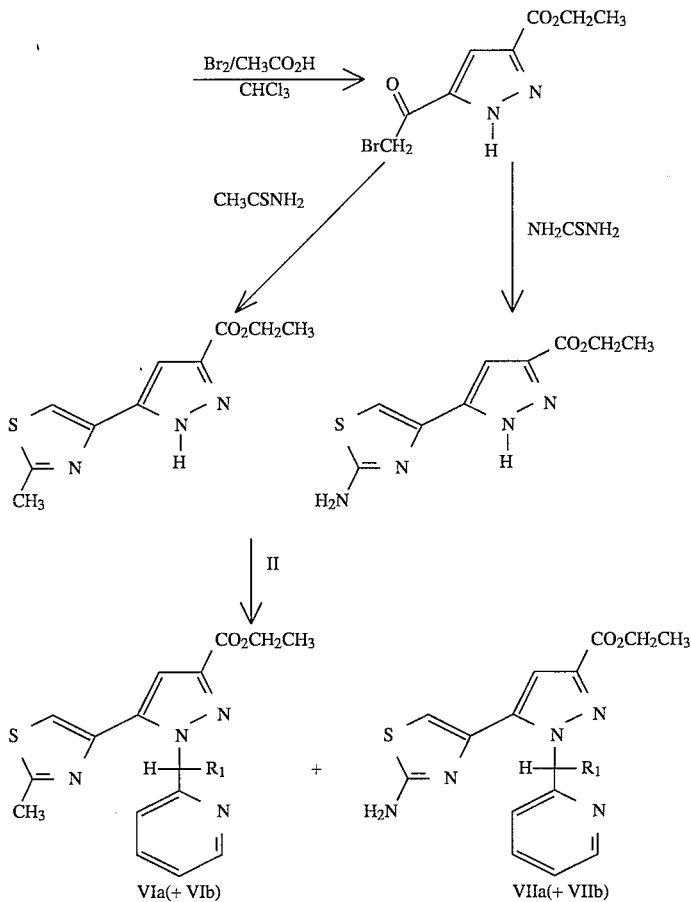

Scheme IV illustrates the synthesis of compounds represented by Formula VIII. Alkylation of the sodium salt of 2-acetylthiazole with diethyl oxalate yields the corresponding ethyl ketoacetate. Reaction of this ethyl ketoacetate with hydrazine yields 3-ethoxycarbonyl-5-(2-thiazolyl)pyrazole. Alkylation, as described above, of 3-ethoxycarbonyl-5-(2-thiazolyl)pyrazole with 2-(alpha-bromoethyl)pyridine (II) yields isomers VIIIa and VIIIb. Compounds can be prepared in a similar manner wherein, in place of the thiazolyl group, $R_2$ or $R_3$ are 2-furyl, 2-thienyl, 2-pyrazyl, 3-pyridyl, or 4-pyridyl radicals, respectively.

Scheme IV

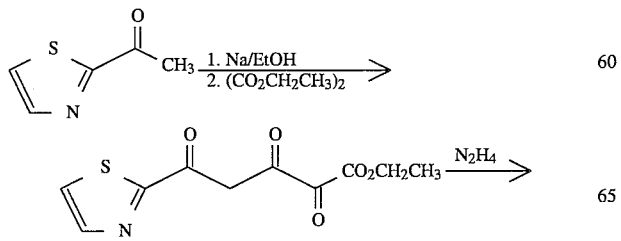

-continued
Scheme IV

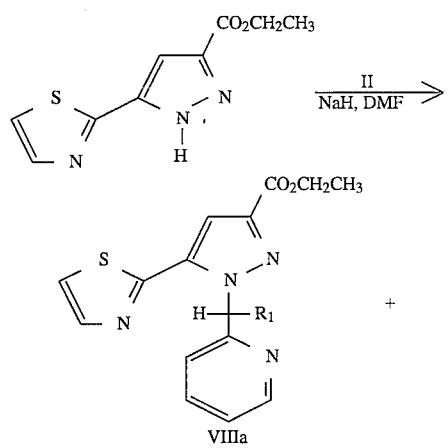

-continued
Scheme IV

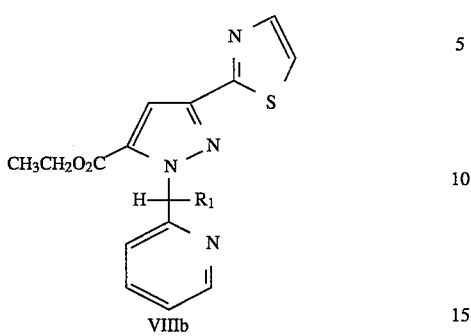

VIIIb which is brominated with trimethylphenylammonium tribromide to afford the corresponding alpha-bromoacetyl derivative. Reaction of the alpha-bromoacetyl derivative with 2-aminopyridine in refluxing ethanol yields 3-ethoxycarbonyl-5-(2-imidazo[1,2a]pyridin-3-yl)pyrazole which is then alkylated to yield isomers XIIa and XIIb.

Scheme V illustrates the synthesis of compounds represented by Formula XI. Reaction of 3,5-pyrazoledicarboxylic acid with acidic ethanol yields the corresponding diethyl ester. Alkylation of the diethyl ester with 2-(alpha-bromoethyl)pyridine (II) yields isomers IXa and IXb. Reaction of isomers IXa and IXb with hydrazine in refluxing ethanol yields isomers Xa and Xb. Reaction of isomers Xa and Xb with ethyl orthoacetate yields isomeric 1,3,4-oxadiazol-2-yl compounds XIa and XIb.

Scheme V

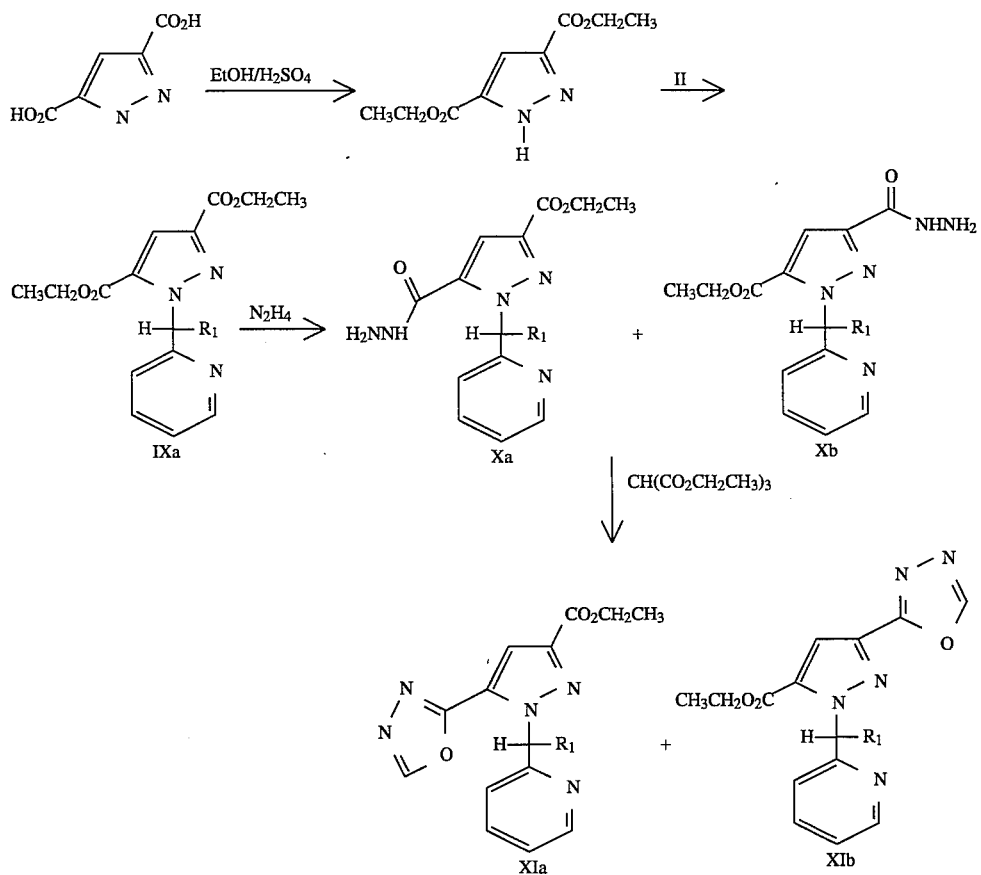

Scheme VI illustrates the synthesis of compounds represented by Formula XII. Reaction of 3-butyne-2-one and ethyl diazoacetate yields 3-ethoxycarbonyl-5-acetylpyrazole Scheme VI

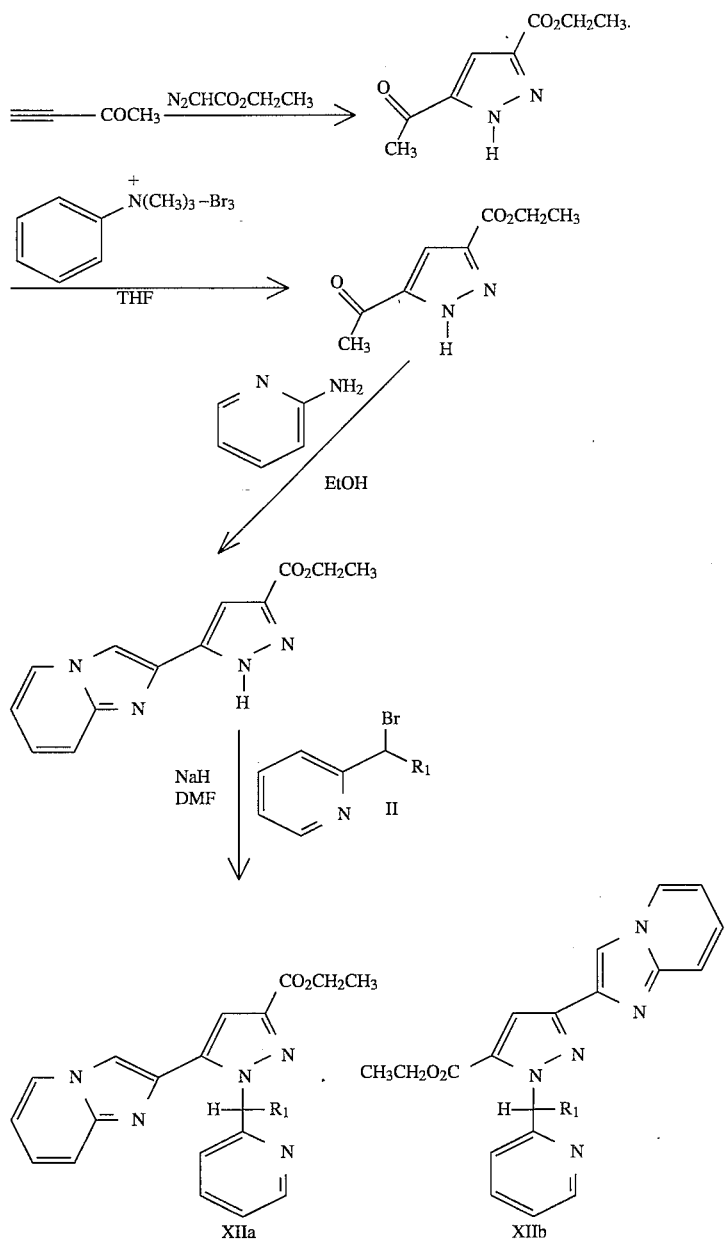

Scheme VII illustrates the synthesis of compounds represented by Formulae XIIIa and XIXb, Reaction of a mixture of thionicotinamide and 3-ethoxycarbonyl-5-(alpha-bromoacetyl)pyrazole in refluxing ethanol yields 3-ethoxycarbonyl-5-(2-(3-pyridinyl)thiazol-4-yl)pyrazole which is alkylated to yield isomers XIIIa and XIIIb. The isomeric (2-pyridinyl)thiazol compounds may be prepared in a manner similar to that set out in Scheme VII by selection of the appropriate thioisonicotinamide.

Scheme VII

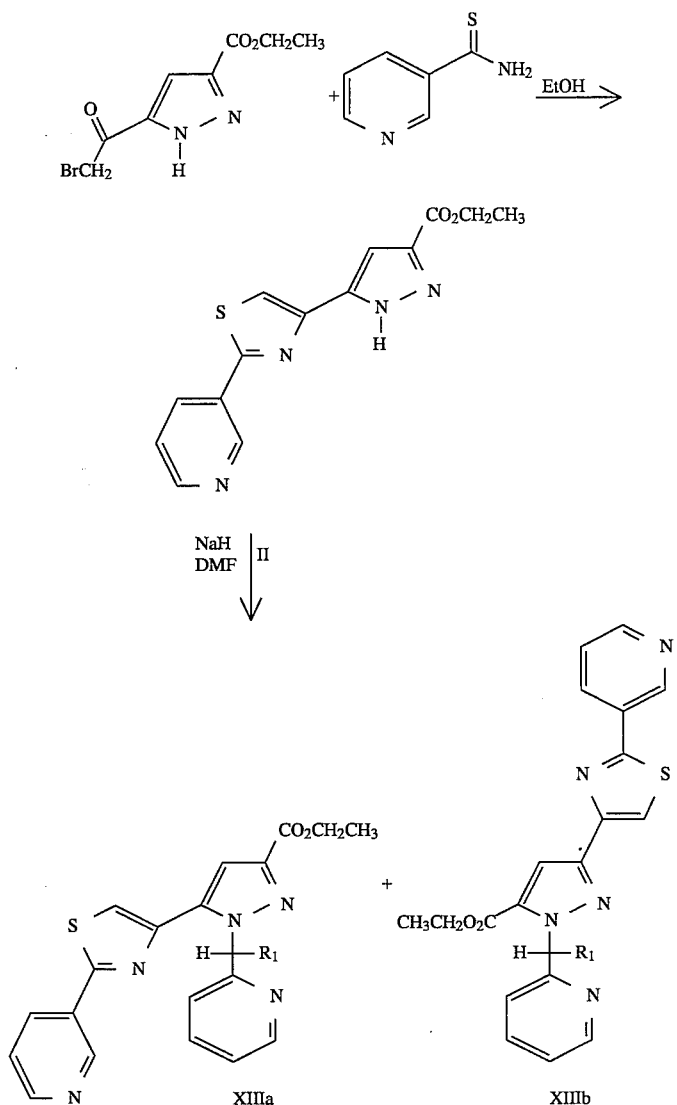

Scheme VIII illustrates the synthesis of compounds represented by Formulas XIV and XV. Reaction of ethyl thiooxamate with 3-ethoxycarbonyl-5-(alpha-bromoacetyl)pyrazole affords 3-ethoxycarbonyl-5-(2-(ethoxycarbonyl)thiazol-4-yl)pyrazole which is alkylated to yield isomers XIVa and XIVb. Alternatively, reaction of 3-ethoxycarbonyl-5-(alpha-bromoacetyl)pyrazole in formamide at 130°–140° C. yields 3-ethoxycarbonyl-5-(4-oxazolyl)pyrazole, which upon alkylation affords isomers XVa and XVb.

Scheme VIII

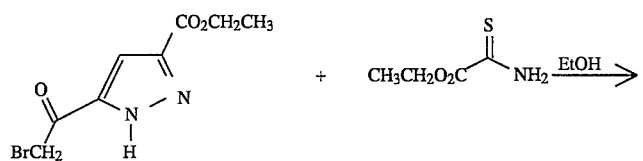

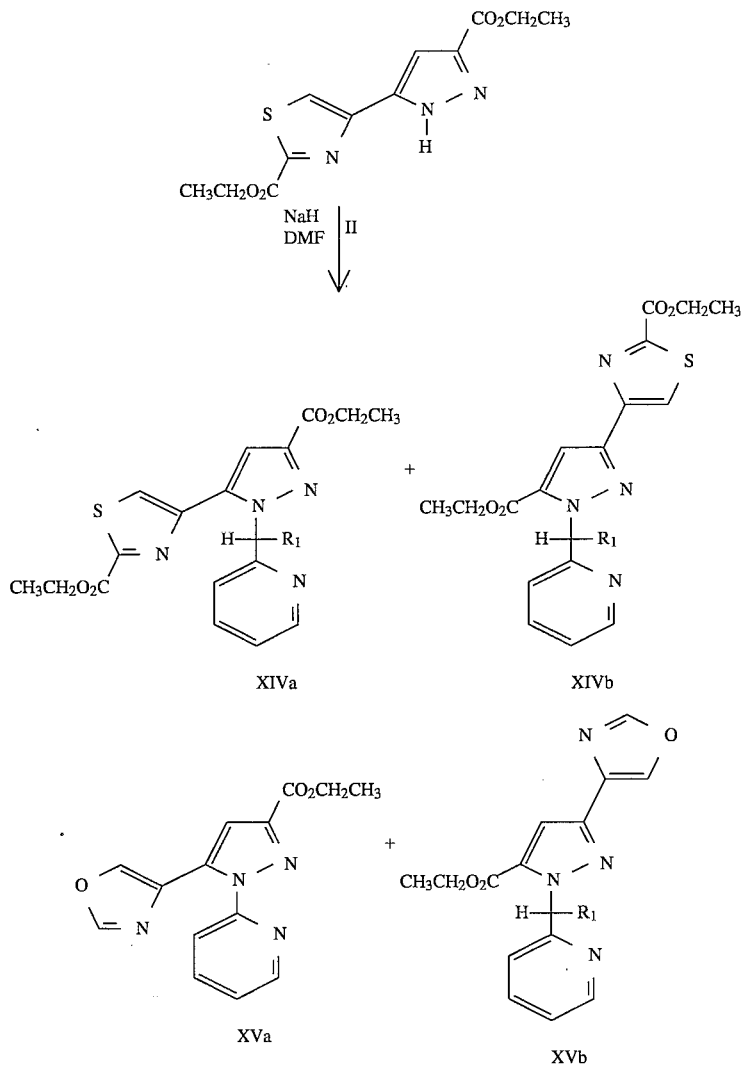

Scheme IX illustrates the synthesis of compounds represented by Formula XVI. Reaction of a mixture of 3-chloro-2,5-pentanedione and formamide in refluxing formic acid yields 4-methyl-5-acetyloxazole. Reaction of the sodium salt of 4-methyl-5-acetyloxazole and diethyl oxalate in ethanol affords the corresponding ketoacetate. Reaction of the ketoacetate with hydrazine in refluxing ethanol yields 3-ethoxycarbonyl-5-[4-(methyl)oxazol-5-yl]pyrazole which is alkylated to yield isomers XXIIa and XXIIb. Substituting triethyl orthoacetate for triethyl orthoformate in the reaction described in Scheme V yields isomeric compounds represented by. Formula XVIIa and XVIIb Scheme IX

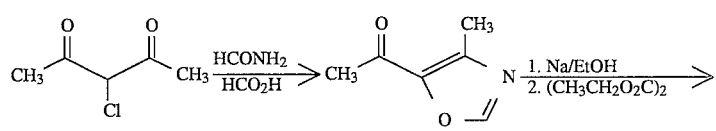

-continued
Scheme IX

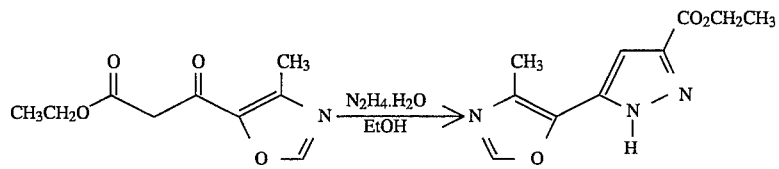

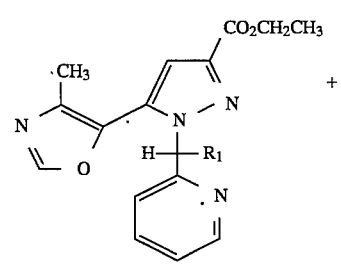
XVIa

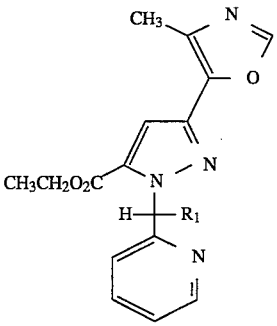
XVIb

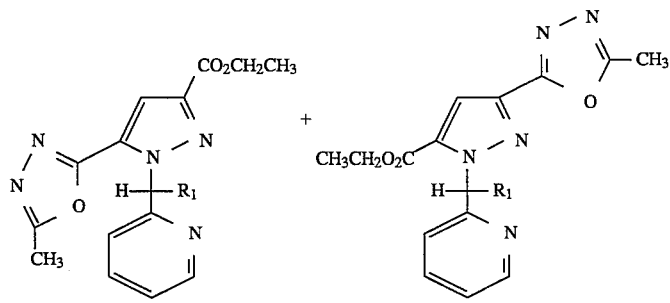
XVIIa    XVIIb

Scheme X illustrates the synthesis of compounds represented by Formula XVIII. Reaction of ethyl nitrite (generated in situ from a mixture of sulfuric acid, sodium nitrite, and ethanol) with 2,5-hexanedione yields 3-acetyl-5-methylisoxazole. Isomeric compounds XXIVa and XXIVb are prepared by the series of reactions outlined previously in Scheme IX.

Scheme X

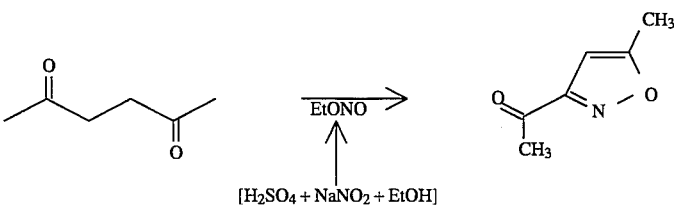

-continued
Scheme X

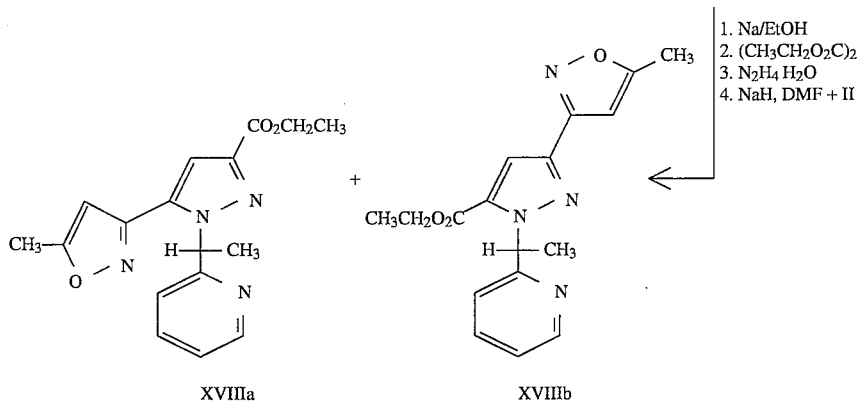

In another embodiment, the present invention is directed to a method for producing anesthesia in a mammal comprising parenterally administering to the mammal an anesthetically effective amount of a compound represented by the Formula (I).

The compounds of the present invention, while effective in the form of the free base, may be formulated and administered in the form of their pharmaceutically acceptable acid addition salts for purposes of stability, convenience of crystallization, increased solubility and the like. These acid addition salts include inorganic acid salts such as hydrochloric, phosphoric, and the like; and organic acid salts such as acetic, oxalic, citric, methanesulfonic, and the like. The preferred acid addition salts are the chloride, oxalate and citrate.

Pharmaceutical compositions containing the compounds of Formula (I) as the free base can be prepared by combining the compounds with a suitable pharmaceutically acceptable carrier such as propylene glycol-alcohol-water, isotonic water, sterile water for injection (USP), Emulphor®-alcohol-water, Cremophor-EL® and the like. Pharmaceutical compositions containing the compounds of Formula (I) as the pharmaceutically acceptable acid addition salts can be prepared by combining the compounds with a suitable pharmaceutically acceptable carrier such as isotonic water, sterile water for injection (USP), alone or in combination with other solubilizing agents such as ethanol, propylene glycol, or other conventional solubilizing agents known to those skilled in the art.

The sterile solutions or suspensions may also include the following adjuvants: a sterile diluent, such as water for injection, saline solution, fixed oils, polyethylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The formulation of these preparations is effected by techniques well known to those of ordinary skill in the art of pharmaceutical compounding. Such preparations may be enclosed in ampules, disposable syringes, or multiple dose vials made of glass or plastic. The compounds of the present invention can be administered to mammals, e.g., animals or humans, in amounts effective to provide the desired anesthetic effect. Since the activity of the compounds and the degree of the desired effect vary, the dosage level of the compound employed will also vary. The actual dosage administered will also be determined by such generally recognized factors as the body weight of the patient and the hypersensitiveness of the particular patient. Thus, the dosage for a particular patient can be as low as about 0.00005 mg/kg, which the practitioner may titrate to the desired effect.

A preferred parenteral administration of the compounds of the present invention is intravenous administration. For intravenous administration, sterile solutions or suspensions as described above should contain at least about 0.1%, by weight, preferably between about 0.1% and about 50%. The exact amount of the inventive compound present in such compositions is such that a suitable dosage level will be obtained. Preferred parenteral dosage units contain from about 0.5 to about 100 milligrams of the inventive compound.

The present invention is further illustrated by the following examples which are presented for purposes of demonstrating, but not limiting, the preparation of the compounds and compositions of this invention. It will be understood that the embodiments described herein are merely exemplary and that a person skilled in the art may make many variations and modifications without departing from the spirit and scope of the invention. All such modifications and variations are intended to be included within the scope of the invention as defined in the appended claims.

EXAMPLE 1

Preparation of a substituted pyrazole intermediate 3,5-Pyrazoledicarboxylic acid diethyl ester (1).

A 3,000 mL round bottom flask was charged with 2,000 mL of absolute ethanol. Dry hydrogen chloride was slowly bubbled through the ethanol solution (chilled with an ice-water bath) for about 45 min. There was then added 200 g of 3,5-pyrazoledicarboxylic acid monohydrate and the mixture was stirred for 72 hours at room temperature. The resulting clear solution was concentrated in vacuo to yield 241.3 g of a colorless viscous residue, 3,5-pyrazoledicarboxylic acid diethyl ester (1), which was used without further purification. NMR: 7.344 (s, 1H), 4.417 (q, 4H), 1.396 (t, 6H).

EXAMPLE 2

Alkylation of the ester formed in Example 1.

A 1,000 mL round bottom flask was charged with 71.0 g of the pyrazole formed in Example 1 and 250 mL of anhydrous dimethyl formamide. A total of 17.4 g of sodium hydride (60% oil suspension) was added portionwise to this solution at 0° C. with stirring. Hydrogen evolution was immediate and lasted about 15 minutes. The reaction mixture was stirred for 1.5 hour at room temperature and then 75.2 g of 1-bromoethyl-2-pyridine was added in one portion. This mixture was stirred overnight at room temperature. The resulting reddish-brown mixture was added into 1,200mL of water and was extracted thoroughly with ethyl acetate (3×600 mL). The combined ethyl acetate solutions were back-washed with water (300 mL), dried over sodium sulfate, and concentrated. The resulting brown residue (~112 g) was recrystallized (diisopropyl ether and hexanes, 1 to 4) to afford the product, 1-[1-(2-pyridyl)ethyl]pyrazole-3,5-dicarboxylic acid diethyl ester (2), 78.1 g, as pale-yellow solids, m.p. 63°–65° C. NMR: 8.551 (dd, 1H), 7.587 (m, 1H), 7.417 (s, 1H), 7.145 (m, 1H), 6.912 (d, 1H), 6.685 (q, 1H), 4.413 (q, 3H), 4.285 (m, 3H) 2.035 (d, 3H), 1.401 and 1.311 (2t, 6H).

EXAMPLE 3

Preparation of a compound of Formula I.

A 500 mL round bottom flask was charged with 87.3 g of the intermediate formed in Example 2 and 200 mL of absolute ethanol. To this solution was added 13.76 g of hydrazine monohydrate. The solution was stirred at 50°–60° C. for 16 hours and then concentrated under vacuum. The residue was treated with 240 mL of triethyl orthoformate and heated to reflux overnight. The resulting mixture was concentrated under vacuum at about 80° C. to remove most of the solvent. The residue was chromatographed (silica gel, eluted with ethyl acetate/hexane, 1/3 to 1/1) to afford 16.4 g of the desired product, 1-[1-(2-pyridyl)ethyl]-3-(1,3,4-oxadiazol-2-yl)pyrazole-5- carboxylic acid ethyl ester (3), as white solids as well as 27.0 g of the starting diester and 8.1 g of the isomer 1-[1-(2-pyridyl)ethyl]-5-(1,3,4-oxadiazol-2-yl)pyrazole-3-carboxylic acid ethyl ester. A portion of the desired compound (10 g) was recrystallized from diisopropyl ether to yield 8.4 g of white crystallines, mp 110°–111° C. NMR: 8.57 (bd, 1H), 8.477 (s, 1H), 7.62 (m, 1H), 7.574 (s, 1H), 7.17 (m, 1H) 7.034 (d, 1H), 6.744 (q, 1H), 4.33 (m, 2H), 2.058 (d, 3H), 1.346 (t, 3H). Crystallization of isomer (8.0 g) from diisopropyl ether afforded 5.3 g of white crystallines, mp 153°–154° C. NMR: 8.513 (bd, 1H), 8.484 (s, 1H), 7.598 (m, 1H), 7.452 (s, 1H), 7.14 (m, 1H), 7.09 (d, 1H), 6.854 (q, 1H), 4.432 (q, 2H), 2.113 (d, 3H), 1.413 (t, 3H).

EXAMPLE 4

Preparation of 5-Formylpyrazole-3-carboxylic acid ethyl ester

A solution of $CrO_3/H_2SO_4/H_2O$ (90 g/60 ml/180 ml) was added dropwise at 15°–20° C. to a cooled mixture of propargyl alcohol (54.0 g) and 2-butanone (100 ml). After the addition, the mixture was stirred at 15° C. for 1 hour and room temperature for 1 hour. It was added with 50 ml of water and separated. The aqueous layer was extracted with ethyl ether (120 ml). The combined organic layer was distilled to afford 20 g of the crude propargyl aldehyde. The crude aldehyde was mixed with ethyl diazoacetate (42.2 g) and toluene (200 ml). The mixture was stirred for overnight at room temperature and 5 hours at 40° C. Filtration afforded 8.4 g of 5-formylpyrazole-3-carboxylic acid ethyl ester as white solids, mp 133°–134° C. NMR: 1.09 (t, 3H), 4.08 (q, 2H), 6.94 (s, 1H, 4-pyrazolyl H), 9.67 (s, 1 H, CHO).

EXAMPLE 5

Preparation of 3-Formyl-1-(1-(2-pyridyl)ethyl)pyrazole-5-carboxylic acid ethyl ester To a mixture of 5-formylpyrazole-3-carboxylic acid ethyl ester (5.42 g) and anhydrous dimethyl formamide (80 ml), 1.41 g of 60% sodium hydride oil suspension were added at 0° C. After 30 minutes, 6.30 g of 2-(1-bromoethyl)pyridine were added at 0° C. The mixture was stirred overnight at room temperature and 120 ml of water was added thereto. The mixture was extracted with ethyl acetate (3×300 ml). The combined organic solution was dried over sodium sulfate and concentrated. The residue was chromatographed (silica gel, Hex/EtOAc 2/1) to afford 4.0 g of 3-formyl-1-(1-(2-pyridinyl)ethyl)pyrazole-5-carboxylic acid ethyl ester as a viscous oil. NMR: 1.33 (t, 3H), 2.01 (d, 3H), 4.29 (m, 2H), 6.73 (q, 1H), 7.40 (s, 1H, 4-pyrazolyl H) 7.06, 7.19, 7.63, 8.57 (4 m, 4H, pyridyl H's), 10.04 (s, 1H, CHO). Also obtained was 535 mg of 5-formyl-1-(1-(2-pyridyl)ethyl)pyrazole-3-carboxylic acid ethyl ester as a viscous oil. NMR: 1.41 (t, 3H), 2.05 (d, 3H), 4.42 (q, 2H), 5.51 (q, 1H), 7.46 (s, 1H, 4-pyrazolyl H), 7.07, 7.17, 7.61, 8.54 (4 m, 4H, pyridyl H's), 9.88 (s, 1H, CHO).

EXAMPLE 6

Preparation of 1-(1-(2-Pyridinyl)ethyl)-3-(oxazol-5-yl)pyrazole-5-carboxylic acid ethyl ester A mixture was prepared by 3-formyl-1-(1-(2-pyridinyl)ethyl)pyrazole-5-carboxylic acid ethyl ester (1.65 g), tosylmethyl isocyocyanide (1.18 g), potassium carbonate (0.78 g), and ethanol (40 ml). The resulting mixture was refluxed for 40 hours, concentrated and the residue extracted with 30 ml of toluene. The toluene solution was loaded to a column (silica gel) and chromatographed (EtOAc/Hex 1/2) to afford 0.38 g of 1-(1-(pyridin-2-yl)ethyl)-3-(oxazol-5-yl)pyrazole-5-carboxylic acid ethyl ester as a clear viscous oil. NMR: 1.33 (t, 3H), 2.03 (d, 3H), 4.29 (m, 2H), 6.68 (q, 1H), 7.16, 7.43, 7.92 (3s, 3H, 4-pyrazolyl and oxazolyl H's), 6.96, 7.15, 7.59, 8.57 (4 m, 4H, pyridinyl H's).

EXAMPLE 7

Preparation of 5-(2-Pyridinyl)pyrazole-3-carboxylic acid ethyl ester

A mixture of 2-ethynylpyridine (10.3 g), ethyl diazoacetate (11.6 g), and toluene (100 ml) was stirred at 85° C. for 36 hours. The resulting mixture was rotavaped and the residue recrystallized with ethanol (50ml) to afford 9.81 g of 5-(2-pyridinyl)pyrazole-3-carboxylic acid ethyl ester as tan crystallines, mp 103°–105° C. NMR: 1.43 (t, 3H), 4.40 (q, 2H), 7.32 (s, 1H, 4-pyrazolyl H), 7.30, 7.78, 8.66 (3 m, 4H, pyridinyl H's).

EXAMPLE 8

Preparation of 1-(1-(2-pyridinyl)ethyl)-3-(2-pyridinyl)pyrazole-5-carboxylic acid ethyl ester To a stirred mixture of 5-(2-pyridinyl)pyrazole-3-carboxylic acid ethyl ester (4.34 g) and anhydrous dimethylformamide (40 ml) at room temperature, 1.92 g of 60% sodium hydride oil suspension were added. After the bubbling had stopped, 3.60 g of 2-picolyl chloride hydrochloride were added. The resulting mixture was stirred at 50° C. overnight, poured into 300 ml of water and extracted with ethyl acetate (2×300 ml). The organic solution was dried over sodium sulfate and rotavaped. The residue was chromatographed (silica gel, EtOAc)to afford 1.93 g of 1-(1-(2-pyridinyl)ethyl)-3-(2-pyridinyl)pyrazole-5-carboxylic acid ethyl ester, as a viscous oil. NMR: 1.31 (t, 3H), 4.29 (q, 2H), 6.00 (s, 2H, 1-pyrazolyl CH$_2$), 7.59 (s, 1H, 4-pyrazolyl H), 6.85, 7.16, 7.32. 7.81, 7.99, 8.57, 8.65 (8 m, 8H, pyridinyl H's). The column also yielded 0.58 g of 1-(1-(2-pyridinyl)ethyl)-5-(2-pyridinyl)pyrazole-3-carboxylic acid ethyl ester, as a viscous oil. NMR: 1.42 (t, 3H), 4.45 (q, 2H), 6.20 (s, 2H, 1-pyrazolyl CH$_2$), 7.26 (s, 1H, 4-pyrazolyl H), 6.74, 7.09, 7.19, 7.51, 7.61, 7.72, 8.49, 8.53 (8 m, 8H, pyridinyl H's).

EXAMPLE 9

Preparation of 5-Acetylpyrazole-3-carboxylic acid ethyl ester

A 500 ml Erlenmeyer flask was charged with 25.0 g of 3-butyne-2-one and ethyl ether (200 ml). To the resulting solution, 41.9 g of ethyl diazoacetate were added slowly with stirring. After 30 minutes of stirring, the ether solution began refluxing by itself. After stirring for 1 hour, the mixture was chilled at 0° C. for 1 hour and filtered to yield 28.5 g of 5-acetylpyrazole-3-carboxylic acid ethyl ester as white solids, mp 114°–115° C. NMR: 1.42 (t, 3H), 2.62 (s, 3H), 4.44 (q, 2H), 7.36 (s, 1H).

EXAMPLE 10

Preparation of 5-(2Bromoacetyl)pyrazole-3-carboxylic acid ethyl ester

A 100ml flask was charged with 27.8 g of 5-acetylpyrazole-3-carboxylic acid ethyl ester and 40 ml of tetrahydrofuran. To this mixture, 56.4 g of phenyltrimethylammonium tribromide were added. The resulting red mixture was stirred at room temperature for 1 hour and poured into 600 ml of water. The resulting mixture was filtered and the solids were washed with more water. The solids were collected, air-dried and recrystallized from 1:1 mixture of diisopropyl ether and hexanes (300ml) to afford 33.1 g of 5-(2-bromoacetyl)pyrazole-3-carboxylic acid ethyl ester as white solids, mp 174°–176° C. NMR: 1.42 (t, 3H), 4.44 (q, 2H), 4.57 (s, 2H), 7.4 (s, 1H).

EXAMPLE 11

Preparation of 5-(2-Methylthiazol-4-yl)pyrazole-3-carboxylic acid ethyl ester

A mixture of 5-(2-bromoacetyl)pyrazole-3-carboxylic acid ethyl ester (5.30 g), thioacetamide (1.60 g), and ethanol (100 ml) was stirred at 60° C. for 30 minutes and concentrated. The residue was dissolved in 50 ml of 2N HCl solution, and washed with ethyl ether (2×50 ml). The aqueous solution was separated and neutralized with solid NaHCO$_3$. The mixture was then extracted with ethyl acetate (233 100 ml). The ethyl acetate solution was dried over sodium sulfate and concentrated to afford 3.46 g of 5-(2-methylthiazol-4-yl)pyrazole-3-carboxylic acid ethyl ester as pale yellow solids, mp 141–142° C. NMR: 1.41 (t, 3H), 2.78 (s, 3H, thiazolyl methyl), 4.42 (q, 2H), 7.15 (s, 1H, thiazolyl H), 7.47 (s, 1H, 4-pyrazolyl H).

EXAMPLE 12

Preparation of 5-(2-Aminothiazol-4-yl)pyrazole-3-carboxylic acid-ethyl ester

A mixture of 5-(2-bromoacetyl)pyrazole-3-carboxylic acid ethyl ester (6.2 g), thiourea (1.8 g), and ethanol (100 ml) was stirred at 60° C. for 30 minutes and concentrated. The residue was dissolved in 100 ml of 1N HCl solution, and washed with ethyl ether (2×100 ml). The aqueous solution was neutralized with NaHCO$_3$. The resulting precipitates were collected through a filtration to afford 4.05 g of 5-(2-aminothiazol-4-yl)pyrazole-3-carboxylic acid ethyl ester as brown solids, mp 205°–207° C. NMR: 1.40 (t, 3H), 4.39 (q, 2H), 5.8 (bs, 2H), 6.85 (s, 1H), 7.03 (s, 1H).

EXAMPLE 13

Preparation of 2,4-diketo-4-(thiazol-2-yl)butyric acid ethyl ester

To a sodium ethoxide solution (prepared from 150 ml of ethanol and 4.2 g of sodium) at 0° C., a mixture of diethyl oxalate (22.98 g) and acetylthiazole (20.07 g) was added dropwise. The resulting mixture was stirred at room temperature for 2 hours and concentrated. The residue was treated with 100 ml of water and neutralized with 6N HCl. Filtration afforded 25.8 g of 2,4-diketo-4-(thiazol-2-yl)butyric acid ethyl ester as brown solids. NMR: 1.46 (t, 3H), 4.49 (q, 2H), 7.27 (s, 1H), 7.65, 8.04 (2d, 2H, thiazolyl H's).

EXAMPLE 14

Preparation of 5-(3Thiazol-2-yl)pyrazole-3-carboxylic acid ethyl ester

A mixture of 2,4-diketo-4-(thiazol-2-yl)butyric acid ethyl ester (9.88 g), hydrazine hydrate (1.74 g), and ethanol (25 ml) was refluxed for one hour, concentrated and the residue chromatographed (silica gel, EtOAc/Hex ½) to afford 2.58 g of 5-(thiazol-2-yl)pyrazole-3-carboxylic acid ethyl ester. NMR: 1.42 (t, 3H), 4.44 (q, 2H), 7.37 (s, 1H, 4-pyrazolyl H), 7.40, 7.75 (2d, 2H, thiazolyl H's).

EXAMPLE 15

Preparation of 1-(1-(2-Pyridinyl)ethyl)-3-(thiazol-2-yl)pyrazole-5-carboxylic acid ester ethyl and 1-(1-(2-pyridinyl)5-(thiazol-2-yl)pyrazole-3-carboxylic acid ethyl ester To a mixture of 2.58 g of 5-(thiazol-2-yl)pyrazole-3-carboxylic acid ethyl ester and 50 ml of anhydrous dimethylformamide, 0.53 g of a 60% NaH oil suspension was added at 0° C. After 20 minutes, 2.36 g of 2-(1-bromo)ethylpyridine were added and the resulting mixture was stirred at 60° C. for 4.5 hrs, poured into 500 ml of water, and extracted with ethyl acetate (3×250 ml). The separated organic layers were dried over sodium sulfate and concentrated. The residue was chromatographed (silica gel, EtOAc/Hex ¼ to ½) to afford 1.87 g of 1-(1-(2-pyridinyl)ethyl-3-(thiazol-2-yl)pyrazole 5-carboxylic acid ethyl ester, as a viscous oil. NMR: 1.32 (t, 3H), 2.04 (d, 3H), 4.30 (m, 2H), 6.68 (q, 1H), 7.47 (s, 1H, 4-pyrazolyl H), 7.32, 7.85 (2d, 2H, thiazolyl H's), 6.94, 7.15, 7.59, 8.58 (4 m, 4H, pyridyl H's). The column also yielded 0.25 g of 1-(1(1- (2-pyridinyl)ethyl)-5-(thiazol-2-yl)pyrazole-3-carboxylic acid ethyl ester, as a viscous oil. NMR: 1.41 (t, 3H), 2.08 (d, 3H), 4.43 (q, 2H), 7.24 (s, 1H, 4-pyrazolyl H), 7.37, 7.84 (2d, 2H, thiazolyl H's), 6.95, 7.11, 7.55, 8.53 (4 m, 5H, pyridyl H's and methine H).

EXAMPLE 16

Preparation of 3-Ethoxycarbonyl-5(2-imidazo[1,2a]pyridin-3-yl)pyrazole

A mixture of 3-(2-bromoacetyl)pyrazole-3-carboxylic acid ethyl ester (10.42 g), 2-aminopyridine (3.35 g), and ethanol (50 ml) was refluxed for 16 hours, concentrated, treated with 150 ml of water, and neutralized with sodium bicarbonate. The mixture was filtered to afford 5.72 g of 3-ethoxycarbonyl-5-(2-imidazo[1,2a]pyridin-3-yl)pyrazole as white solids, mp 237°–239° C. (decomp.). NMR: 1.35 (t, 3H), 4.35 (q, 2H), 6.77, 7.17, 7.57, 8.11 (4 m, 5H, imidazopyridinyl H's), 7.95 (s, 1H, 4-pyrazolyl H).

EXAMPLE 17

Preparation of 3-Ethoxycarbonyl-5-(2-(3-pyridinyl)thiazol-4-yl)pyrazole

A mixture of 3-(2-bromoacetyl)pyrazole-3-carboxylic acid ethyl ester (7.00 g), thionicotinamide (3.51 g), and ethanol (50 ml) was refluxed for 16 hours. The resulting mixture was poured into 400 ml of water, and neutralized with 10 g of sodium bicarbonate. Filtration afforded 5.82 g of 3-ethoxycarbonyl-5-(2-(3-pyridinyl)thiazol-4-yl)pyrazole as yellow solids, mp 105°–107° C. NMR: 1.43 (t, 3H), 4.44 (q, 2H), 7.26 (s, 1H, 5-thiazolyl H), 7.70 (s, 1H, 4-pyrazolyl H), 7.42, 8.30, 8.73, 9.27 (4 m, 4H, pyridinyl H's).

EXAMPLE 18

Preparation of 3-Ethoxycarbonyl-5-(2-ethoxylcarbonylthiazol-4-yl)pyrazole

A mixture of 3-(2-bromoacetyl)pyrazole-3-carboxylic acid ethyl ester (1.93 g), ethyl thiooxamate (1.02 g) and ethanol (40 ml) was refluxed for 1 hour, concentrated and the residue partitioned between ethyl acetate (100 ml) and 5% sodium bicarbonate solution (100 ml). The organic layer was separated, dried over sodium sulfate, and concentrated. The residue was chromatographed (silica gel, EtOAc/Hex ⅓ ) to afford 1.59 g of 3-ethoxycarbonyl-5-(2-ethoxycarbonylthiazol-4-yl)pyrazole as white solids, mp 104°–106° C. NMR: 1.42, 1.46 (2t, 6H), 4.43, 4.52 (2q, 4H), 7.31, 7.93 (2s, 2H).

EXAMPLE 19

Preparation of 3-Ethoxycarbonyl-5-(oxazol-4-yl)pyrazole

A mixture of 3-(2-bromoacetyl)pyrazole-3-carboxylic acid ethyl ester(15.6 g) and formamide (50 ml) was stirred at 140° C. for 30 minutes and poured into 400 ml of water. The resulting mixture was neutralized with sodium bicarbonate, and extracted with ethyl acetate (2×200 ml). The ethyl acetate solution was dried over sodium sulfate and concentrated. The residue was chromatographed (silics gel, EtOAc/Hex ⅓ to ½ ) to yield 2.31 g of 3-ethoxycarbony-5-(oxazol-4-yl)pyrazole. NMR: 1.40 (t, 3H), 4.42 (q, 2H), 7.16 (s, 1H, 4-pyrazolyl H), 8.09, 8.16 (2bs, 2H, oxazolyl H's).

EXAMPLE 20

Preparation of 5-Acetyl-4-methyloxazole

A mixture of 3-chloro-2,4-pentanedione (26.8 g), formamide (18.0 g), and formic acid (50.0 g) was heated in a 140° C. oil bath and refluxed for 4 hours. The resulting dark mixture was poured into 100 ml of water, basified with 50% NaOH solution, and saturated with NaCl. The mixture was extracted with ethyl ether (3×100 ml). The ether solution was dried over sodium sulfate and concentrated. The residue was vacuum-distilled to yield 6.59 g of 5-acetyl-4-methyloxazole as a colorless liquid, 84° C. (15 torr). NMR: 2.51 (s, 3H), 2.52 (s, 3H), 7.85 (s, 1H).

EXAMPLE 21

Preparation of 2,4-Diketo-4-(4-methyloxazol-5-yl)butyric acid ethyl ester

To a sodium ethoxide solution (2.7 g of sodium and 50 ml of ethanol), a mixture of diethyl oxalate (14.48 g) and 5-acetyl-4-methyloxazole (12.4 g) was added dropwise at 0° C. The resulting mixture as stirred at room temperature for 1.5 hours, and concentrated. The residue was treated with 150 ml of water, and neutralized with 6N HCl. The resulting mixture was filtered to afford 17.5 g of 2,4-diketo-4-(4-methyloxazol-5-yl)butyric acid ethyl ester as white solids. NMR: 1.41 (t, 3H), 2.60 (s, 3H, oxazolyl methyl), 4.40 (q, 2H), 6.93 (s, 1H), 7.99 (s, 1H, 2-oxazolyl H).

EXAMPLE 22

Preparation of 3-Ethoxycarbonyl-5-(4-methyloxazol-5-yl)pyrazole

A mixture of 2,4-diketo4-(4-methyloxazol-5-yl)butyric acid ethyl ester (8.50 g), hydrazine hydrate (1.88 g), and ethanol (100 ml) was refluxed for 3 hours and concentrated. The residue was chromatographed (silica gel, Hex/EtOAc ½) to yield 4.20 g of 3-ethoxycarbonyl-5-(4-methyloxazol-5-yl)pyrazole as tan solids, mp 131°–133° C. (methanol/isopropyl ether). NMR: 1.42 (t, 3H), 2.48 (s, 3H), 4.44 (q, 2H), 7.05 (s, 1H, 4-pyrazolyl H), 7.85 (s, 1H, 2-oxazolyl H). .

EXAMPLE 23

Preparation of 3-Acetyl-5-methylisoxazole

Ethyl nitrate was bubbled slowly into a stirred mixture of acetonyl acetone (42.8 g) and concentrated HCl (4.5 ml) below 50° C. The ethyl nitrite was generated by the dropwise addition of a solution of $NaNO_2$ (54.36 g), ethanol (24 ml), and water (215 ml) to a solution of concentrated sulfuric acid (22 ml), ethanol (24 ml), and water (215 ml). After 4 hours, the resulting mixture was added to 100 ml of saturated $NaHCO_3$ solution. The mixture was saturated with NaCl, and extracted with ethyl ether (2×200 ml). The ether solution was dried over sodium sulfate and concentrated. The residue was vacuum-distilled to afford 25.5 g of 3-acetyl-5-methylisoxazole as a colorless liquid, 74°–75° C. at 12 torr. NMR: 2.49 (s, 3H), 2.63 (s, 3H), 6.36 (s, 1H, 4-isoxazolyl H).

EXAMPLE 24

Preparation of 3-Ethoxycarbonyl-5-(5-methylisoxazol-3-yl)pyrazole

A mixture of 3-acetyl-5-methylisoxazole (37.2 g), hydrazine hydrate (8.27 g), and ethanol (100 ml) was stirred at 50° C. for 16 hours. The mixture was filtered, and the filtrate was concentrated. The residue was chromatographed (silica gel, EtOAc/Hex ½) to afford 5.0 g of 3-ethoxycarbonyl-5-(5-methylisoxazol-3-yl)pyrazole as yellow soilds, mp 149°–151° C. NMR: 1.42 (t, 3H), 2.50 (s, 3H), 4.43 (q, 2H), 6.74 (s, 1H, 4-isoxazolyl H), 7.27 (s, 1H, 4-pyrazolyl H).

EXAMPLE 25

The efficacy of representative compounds of the present invention as anesthetics by intravenous administration was demonstrated as follows. The acid addition salts of the compounds were dissolved in sterile water for injection, U.S.P, to form a solution, the concentration of which varied from 0.001 mg/ml to 5 mg/ml. Mice or rats were used for the tests. The test solution was administered to the test animal intravenously through the lateral tail vein. The animals were observed over a 20 minute period for loss of righting which is defined as the animal remaining in a supine position for 30 seconds. Five to ten mice and three to six rats were utilized for each dosage. The $ED_{50}$ was calculated for each test compound either by linear regression or by a standard computer program utilizing the method of Litchfield and Wilcoxon, J. Pharmacol. Exp. Ther., vol. 96, p. 99 (1949). The $ED_{50}$ values were corrected to compensate for the salts and are reported in Table 1. Since different animals were used, the $ED_{50}$ values in Table 1 are those determined in the mouse except those values marked with an asterisk which were determined in the rat.

TABLE 1

[Structure: pyrazole ring with substituents $R_2$, $R_3$, $R_1$ and a linked aryl group with Y, Z]

| $R_1$ | $R_2$ | $R_3$ | Y | Z | Loss of Righting, $ED_{50}$ (mg/kg) |
|---|---|---|---|---|---|
| H | $CH_3$ | $CO_2Et$ | N | CH | 17.4 |
| H | $CH_3$ | $CO_2Et$ | CH | N | 25.1 |
| H | $CO_2Et$ | $CH_3$ | N | CH | 37.7 |
| H | $CO_2Et$ | $CH_3$ | CH | N | — |
| H | $CO_2Et$ | $CO_2Et$ | N | CH | 6.9 |
| H | $CO_2Et$ | $CO_2Et$ | CH | N | 10.4 |
| $CH_3$ | $CO_2Et$ | $CO_2Et$ | CH | N | 8.6 |
| $CH_3$ | $CO_2Et$ | $CO_2Et$ | N | CH | 1.4 |
| $CH_3$ | $CH_3$ | $CO_2Et$ | N | CH | 9.0 |
| $CH_3$ | $CH_3$ | $CO_2Et$ | CH | N | 21.5 |
| $CH_3$ | $CO_2Et$ | $CH_3$ | N | CH | 6.9 |
| $CH_3$ | $CO_2Et$ | $CH_3$ | CH | N | 26.3 |
| $CH_3$ | H | $CO_2Et$ | N | CH | 31.0 |
| $CH_3$ | $CO_2Et$ | H | N | CH | 34.2 |
| H | $CO_2Et$ | H | CH | N | — |
| H | $CO_2Et$ | H | N | CH | 43.9 |
| $CH_3$ | $CH_2OCOCH_3$ | $CH_3$ | N | CH | 61.1 |
| $CH_3$ | $CO_2Et$ | $CH_2OCH_3$ | N | CH | 19.1 |
| $CH_3$ | $CO_2Et$ | $CH_2CH_3$ | N | CH | 9.4 |
| $CH_3$ | $CH_2CH_3$ | $CO_2Et$ | N | CH | 9.4 |
| $CH_3$ | $CO_2Et$ | $CH_2OCOCH_3$ | N | CH | 28.3 |
| $CH_3$ | $C(=CH_2)CH_3$ | $CO_2Et$ | N | CH | — |
| $CH_3$ | $CO_2Et$ | $C(=CH_2)CH_3$ | N | CH | 8.9 |
| $CH_3$ | $CH_3CO$ | $CO_2Et$ | N | CH | 4.0 |
| $CH_3$ | $CO_2Et$ | $CH_3CO$ | N | CH | 19.7 |
| $CH_3$ | CHO | $CO_2Et$ | N | CH | 9.9 |
| H | CHO | $CO_2Et$ | N | CH | — |
| $CH_3$ | $CO_2Et$ | OH | N | CH | 31.0 |
| $CH_3$ | thiazolyl (N,S) | $CO_2Et$ | N | CH | 3.2 |
| $CH_3$ | $CO_2Et$ | thiazolyl (N,S) | N | CH | — |
| $CH_3$ | thienyl (S) | $CO_2Et$ | N | CH | — |
| $CH_3$ | $CO_2Et$ | thienyl (S) | N | CH | 17.6 |

TABLE 1-continued

[Structure: pyrazole ring with R2 at 3-position, R3 at 5-position, N1 substituted with CH(R1) connected to a phenyl ring bearing a Y=Z group]

| R$_1$ | R$_2$ | R$_3$ | Y | Z | Loss of Righting, ED$_{50}$ (mg/kg) |
|---|---|---|---|---|---|
| CH$_3$ | 3-thienyl | CO$_2$Et | N | CH | — |
| CH$_3$ | CO$_2$Et | 3-thienyl | N | CH | 17.6 |
| CH$_3$ | 2-furyl | CO$_2$Et | N | CH | 1.3 |
| CH$_3$ | CO$_2$Et | 2-furyl | N | CH | — |
| H | 2-furyl | CO$_2$Et | N | CH | 8.9 |
| H | CO$_2$Et | 2-furyl | N | CH | 17.6 |
| H | CO$_2$Et | 2-thienyl | N | CH | 14.3 |
| H | 2-thienyl | CO$_2$Et | N | CH | 28.3 |
| CH$_3$ | oxazolyl | CO$_2$Et | N | CH | 2.8 |
| CH$_3$ | 1,3,4-oxadiazolyl | CO$_2$Et | N | CH | 9.0 |
| CH$_3$ | CO$_2$Et | 1,3,4-oxadiazolyl | N | CH | 7.2* |

TABLE 1-continued

| $R_1$ | $R_2$ | $R_3$ | Y | Z | Loss of Righting, $ED_{50}$ (mg/kg) |
|---|---|---|---|---|---|
| $CH_3$ | 2-pyridyl | $CO_2Et$ | N | CH | 3.5 |
| $CH_3$ | $CO_2Et$ | 2-pyridyl | N | CH | 17.5 |
| $CH_3$ | 4-pyridyl | $CO_2Et$ | N | CH | 12.0 |
| $CH_3$ | 3-pyridyl | $CO_2Et$ | N | CH | 2.3 |
| $CH_3$ | 2-($CO_2Et$)-thiazol-4-yl | $CO_2Et$ | N | CH | 13.6 |
| $CH_3$ | $CO_2Et$ | 2-($CO_2Et$)-thiazol-4-yl | N | CH | 31.6 |
| $CH_3$ | 2-(4-pyridyl)-thiazol-4-yl | $CO_2Et$ | N | CH | 5.7 |
| $CH_3$ | $CO_2Et$ | 2-(4-pyridyl)-thiazol-4-yl | N | CH | 51.4 |
| $CH_3$ | 2-(3-pyridyl)-thiazol-4-yl | $CO_2Et$ | N | CH | 1.1* |
| $CH_3$ | $CO_2Et$ | 2-(3-pyridyl)-thiazol-4-yl | N | CH | — |
| $CH_3$ | imidazo[1,2-a]pyridin-2-yl | $CO_2Et$ | N | CH | 14.3 |

TABLE 1-continued

[Structure: pyrazole with R2, R3, R1 substituents and Y=Z group]

| R1 | R2 | R3 | Y | Z | Loss of Righting, ED50 (mg/kg) |
|---|---|---|---|---|---|
| CH3 | [oxazole-CH3] | CO2Et | N | CH | 1.2* |
| CH3 | CO2Et | [oxazole-CH3] | N | CH | 8.8* |
| CH3 | [oxazole] | CO2Et | N | CH | 7.7 |
| CH3 | CO2Et | [oxazole] | N | CH | 13.4 |
| CH3 | [CH3-oxazole] | CO2Et | N | CH | 4.7 |
| CH3 | CO2Et | [CH3-oxazole] | N | CH | 23.2* |
| CH3 | [CH3-isoxazole-CH3] | CO2Et | N | CH | 9.9 |
| CH3 | CO2Et | [CH3-isoxazole-CH3] | N | CH | 23.7 |
| CH3 | [H3C-isoxazole] | CO2Et | N | CH | 3.8* |
| CH3 | CO2Et | [H3C-isoxazole] | N | CH | 7.2* |
| CH3 | [oxazole-H3C] | CO2Et | N | CH | 1.1* |

TABLE 1-continued

[Structure: pyrazole with R2 at 3-position, R3 at 5-position, N1 connected to CH(R1) linked to phenyl ring with Y=Z]

| R₁ | R₂ | R₃ | Y | Z | Loss of Righting, ED₅₀ (mg/kg) |
|---|---|---|---|---|---|
| CH₃ | CO₂Et | [4-methyl-oxazol-2-yl] | N | CH | 0.85* |
| CH₃ | CO₂Et | [oxazol-2-yl] | N | CH | 0.85* |
| CH₃ | [1-methylpyrrol-2-yl] | CO₂Et | N | CH | 0.95 |
| CH₃ | CO₂Et | [1-methylpyrrol-2-yl] | N | CH | 6.2 |
| CH₃ | CO₂Et | [1-methylpyrrol-3-yl] | N | CH | 4.2* |
| CH₃ | [3-methyl-1,2,4-oxadiazol-5-yl] | CO₂Et | N | CH | 0.79* |
| H | [pyridin-3-yl] | CO₂Et | N | CH | 7.0* |
| H | CO₂Et | [pyridin-3-yl] | N | CH | 17.7* |
| CH₃ | [6-methylpyridin-2-yl] | CO₂Et | N | CH | 1.6* |
| H | [pyridin-2-yl] | CO₂Et | N | CH | 5.1* |
| CH₃ | [2-aminophenyl] | CO₂Et | N | CH | 0.81* |

TABLE 1-continued
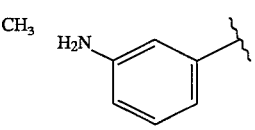
| $R_1$ | $R_2$ | $R_3$ | Y | Z | Loss of Righting, $ED_{50}$ (mg/kg) |
|---|---|---|---|---|---|
| $CH_3$ | 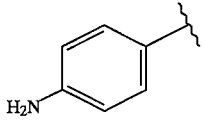 | $CO_2Et$ | N | CH | 0.53* |
| $CH_3$ | 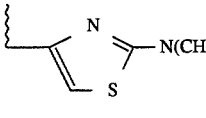 | $CO_2Et$ | N | CH | 2.7* |
| $CH_3$ | 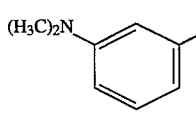 | $CO_2Et$ | N | CH | — |
| $CH_3$ | 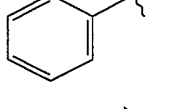 | $CO_2Et$ | N | CH | 1.5* |
| $CH_3$ | 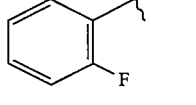 | $CO_2Et$ | N | CH | 2.8* |
| H | 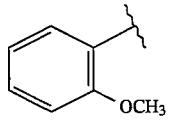 | $CO_2Et$ | N | CH | — |
| H | 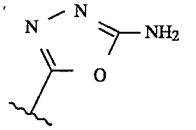 | $CO_2Et$ | N | CH | — |
| $CH_3$ | 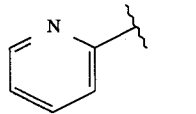 | $CO_2Et$ | N | CH | — |
| H | 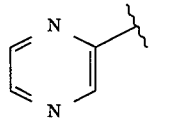 | $CO_2Et$ | CH | N | 30.5* |
| $CH_3$ |  | $CO_2Et$ | N | CH | 1.5* |

TABLE 1-continued

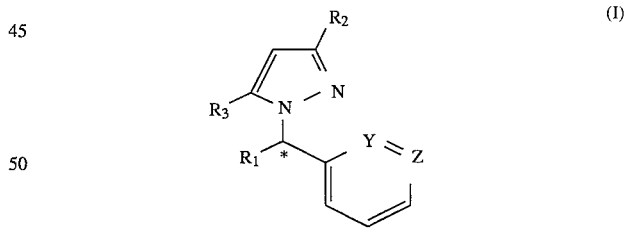

| $R_1$ | $R_2$ | $R_3$ | Y | Z | Loss of Righting, $ED_{50}$ (mg/kg) |
|---|---|---|---|---|---|
| $CH_3$ | $COCO_2Et$ | $CO_2Et$ | N | CH | 2.86* |
| $CH_3$ | $CONHC_3H_7$ | $CONHC_3H_7$ | N | CH | — |
| $CH_3$ | $CONHC_3H_7$ | $CO_2Et$ | N | CH | 1.8* |
| $CH_3$ | $CO_2Et$ | $CONHC_3H_7$ | N | CH | — |

We claim:

1. A compound represented by the Formula:

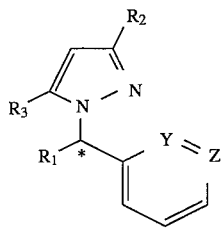

including geometric and optically active isomeric forms, and pharmaceutically acceptable acid addition salts thereof, wherein:

one of Y and Z is nitrogen, and the other is CH;

$R_1$ is hydrogen or lower-alkyl;

$R_2$ and $R_3$ are selected from the group consisting of hydrogen, —CHO, lower-alkylcarbonyl, lower-alkoxycarbonyl, lower-alkylaminocarbonyl, lower-alkyl, lower-alkenyl, lower-alkoxy-lower-alkenyl, lower-alkylcarbonyloxymethyl, substituted and unsubstituted heterocyclic rings, and substituted or unsubstituted aryl groups, wherein the symbol * represents a carbon atom which may be asymmetric and with the proviso that at least one of $R_2$ and $R_3$ is other than hydrogen and methyl.

2. The compound according to claim 1, wherein Y is nitrogen.

3. The compound according to claim 1, wherein $R_1$ is hydrogen or methyl.

4. The compound according to claim 1, wherein at least one of $R_2$ and $R_3$ is a substituted or unsubstituted heterocyclic ring selected from the group consisting of furanyl, thiophenyl, pyrrolyl, oxazolyl, isoxazolyl, thiazolyl, 2-(2-pyridinyl)thiazolyl, 2-(3-pyridinyl)thiazolyl, 1,2,4-oxadiazolyl, 1,3,4-oxadiazolyl, pyridinyl, and imidazo[1,2-a]pyridinyl.

5. The compound according to claim 4, wherein at least one of $R_2$ and $R_3$ is a substituted or unsubstituted heterocyclic ring selected from the group consisting of furan-2-yl, furan-3-yl, thiophen-2-yl, thiophen-3-yl, pyrrol-2-yl, pyrrol-3-yl, (N-methyl)pyrrol-2-yl, (N-methyl)pyrrol-3-yl, oxazol-2-yl, oxazol-4-yl, oxazol-5-yl, isoxazol-3-yl, isoxazol-4-yl, isoxazol-5-yl, thiazol-5-yl, 2-(carboethoxy)thiazol-5-yl, 2-(2- pyridinyl)thiazol-5-yl, 2-(3-pyridinyl)thiazol-5-yl, 1,2, 4-oxadiazol-5-yl, 1,3,4-oxadiazol-5-yl, pyridin-2-yl, pyridin-3-yl, pyridin-4-yl, and imidazo[1,2-a]pyridin-2-yl.

6. The compound according to claim 5, wherein one of $R_2$ and $R_3$ is 1,3,4-oxadiazol-5-yl or pyridin-3-yl.

7. The compound according to claim 1, wherein one of $R_2$ and $R_3$ is phenyl or phenyl substituted with one or more members selected from the group consisting of halogen, lower-alkyl, and lower-alkoxy.

8. The compound according to claim 1, wherein one of $R_2$ and $R_3$ is ethoxycarbonyl.

9. The compound according to claim 1, which comprises 1-[1-(2-pyridyl)ethyl]-3-(1,3,4-oxadiazol-2-yl) pyrazole-5-carboxylic acid ethyl ester, and the pharmaceutically acceptable acid addition salts thereof.

10. The compound according to claim 1, which comprises 1-[(2-pyridyl)methyl]-3-(2-pyridyl) pyrazole-5-carboxylic acid ethyl ester, and the pharmaceutically acceptable acid addition salts thereof.

11. A method for producing anesthesia in a mammal comprising intravenously administering to the mammal an anesthetically effective amount of a compound represented by the Formula:

(I)

including geometric and optically active isomeric forms, and the pharmaceutically acceptable acid addition salts thereof, wherein:

one of Y and Z is nitrogen, and the other is CH;

$R_1$ is hydrogen or lower-alkyl;

$R_2$ and $R_3$ are selected from the group consisting of hydrogen, —CHO, lower-alkylcarbonyl, lower-alkoxycarbonyl, lower-alkylaminocarbonyl, lower-alkyl, lower-alkenyl, lower-alkoxy-lower-alkenyl, lower-alkylcarbonyloxymethyl, substituted and unsubstituted heterocyclic rings lower-alkyl, and substituted or unsubstituted aryl, wherein the symbol * represents a carbon atom which may be asymmetric and at least one of $R_2$ and $R_3$ is other than hydrogen.

12. The method according to claim 11, wherein Y is nitrogen.

13. The method according to claim 11, wherein $R_1$ is hydrogen or methyl.

14. The method according to claim 11, wherein at least one of $R_2$ and $R_3$ is a substituted or unsubstituted heterocyclic ring selected from the group consisting of furanyl, thiophenyl, pyrrolyl, oxazolyl, isoxazolyl, thiazolyl, 2-(2-pyridinyl)thiazolyl, 2-(3-pyridinyl)thiazolyl, 1,2,4-oxadiazolyl, 1,3,4-oxadiazolyl, pyridinyl, and imidazo[1,2a]pyridinyl.

15. The method according to claim 14, wherein at least one of $R_2$ and $R_3$ is a substituted or unsubstituted heterocyclic ring selected from the group consisting of furan-2-yl, furan-3-yl, thiophen-2-yl, thiophen-3-yl, pyrrol-2-yl, pyrrol-3-yl, (N-methyl)pyrrol-2-yl, (N-methyl)pyrrol-3-yl, oxazol-2-yl, oxazol-4-yl, oxazol-5-yl, isoxazol-3-yl, isoxazol-4-yl, isoxazol-5-yl, thiazol-5-yl, 2-(carboethoxy)thiazol-5-yl, 2-(2-pyridinyl)thiazol-5-yl, 2-(3-pyridinyl)thiazol-5-yl, 1,2,4-oxadiazol-5-yl, 1,3,4-oxadiazol-5-yl, pyridin-2-yl, pyridin-3-yl, pyridin-4-yl, and imidazo[1,2-a]pyridin-2-yl.

16. The method according to claim 15, wherein one of $R_2$ and $R_3$ is 1,3,4-oxadiazol-5-yl or pyridin-3-yl.

17. The method according to claim 11, wherein one of $R_2$ and $R_3$ is phenyl or phenyl substituted with one or more members selected from the group consisting of halogen, lower-alkyl, and lower-alkoxy.

18. The method according to claim 11, wherein one of $R_2$ and $R_3$ is ethoxycarbonyl.

19. The method according to claim 11, wherein the compound is 1-[1-(2-pyridyl)ethyl]-3-(1,3,4-oxadiazol-2-yl) pyrazole-5-carboxylic acid ethyl ester or a pharmaceutically acceptable acid addition salt thereof.

20. The method according to claim 11, wherein the compound is 1-[(2pyridyl)methyl]-3-(2-pyridyl) pyrazole-5-carboxylic acid ethyl ester or a pharmaceutically acceptable acid addition salt thereof.

* * * * *